United States Patent [19]
Pei et al.

[11] Patent Number: 5,330,994
[45] Date of Patent: Jul. 19, 1994

[54] TETRAHYDROPYRIDINE ISOXAZOLINE DERIVATIVES

[75] Inventors: Yazhong Pei, Ann Arbor; Haile Tecle, Ypsilanti, both of Mich.

[73] Assignee: Warner-Lambert Company, Morris Plains, N.J.

[21] Appl. No.: 856,603

[22] Filed: Mar. 24, 1992

[51] Int. Cl.$^5$ .................. C07D 401/04; A61K 31/44
[52] U.S. Cl. ................................ 514/340; 514/326; 546/275; 546/208
[58] Field of Search ............... 546/275, 208; 514/340, 514/326

[56] References Cited

FOREIGN PATENT DOCUMENTS 0316718  5/1959  European Pat. Off. .

OTHER PUBLICATIONS

The Condensed Chemical Dictionary 10th Edition by Hawley, p. 90, 1981.
Clark et al. Principles of Psychopharmacology 1970, pp. 166–167.
Trends in Neuroscience, 10(11):444–446 (1987), Quirion et al., "Classification and nomenclature of phencyclidine ... ".
Clinical Neuropharmacology, 11(2):105–119, S. Deutsch et al., "The Sigma Receptor: A Novel Site Implicated . . .".
Molecular Pharmacology, 32:772–784, (1987), B. Largent et al., "Structural Determinants of σ Receptor Affinity".
Pharmacological Reviews, 42(4):355–402, (1990), J. Walker, et al., "Sigma Receptors: Biology and Function".
Drug Development Research, 11:65–70 (1987), D. Taylor et al., "Potential Antipsychotic BMY 14802 Selectively ...".
Clinical Neuropharmacology, 11(6):565, (1988), K. Jansen, "The Sigma Receptor and Movement Disorders".
Neurology, 38:961–965 (1988), J. Walker et al., "Evidence for a role of haloperidol-sensitive σ-'opiate' ...".
European J. of Pharmacology, 147:153–154 (1988), W.

Bowen et al., "Altered haloperidol-sensitive σ receptors ...".
Science, 2240:219–221 (1988), T. Su et al., "Steroid Binding at σ Receptors Suggest a Link Between ...".
European J. of Pharmacology, 148:467–470 (1988), T. Su et al., "Correlation of inhibitory potencies of putative . . .".
Soc. for Neuroscience Abstracts, 13(2):1437 (1987), S. Wolfe et al., "Sigma Receptors in Human Peripheral . . .".
J. Pharmacology and Experimental Therapeutics, 197(3):517–532, W. Martin et al., "The Effects of Morphine ...".
Society for Neuroscience Abstracts, 17:333 (1991), L. Cook et al., "The Pharmacology of a Sigma ...".

Primary Examiner—Jane T. Fan
Attorney, Agent, or Firm—Michael J. Atkins; Charles W. Ashbrook

[57] ABSTRACT

A novel compound of the following formulas useful in treating immune-related diseases, inflammation, stoke, epilepsy, dystonias, psychoses, anxiety, and depression:

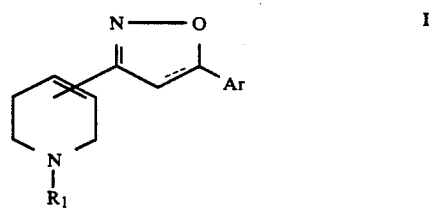

I

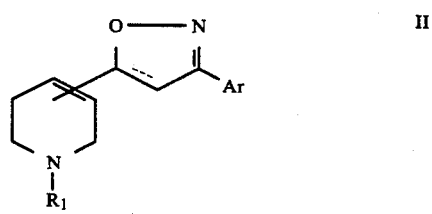

II

12 Claims, No Drawings

TETRAHYDROPYRIDINE ISOXAZOLINE DERIVATIVES

FIELD OF INVENTION

The present invention relates to novel compounds which have affinity for the sigma binding site, rendering said compounds useful in treating conditions of the central nervous system including depression, psychoses, stroke, epilepsy, dystonias, anxiety, inflammatory diseases, and other immune related diseases.

BACKGROUND OF THE INVENTION

The classification and nomenclature of phencyclidine and sigma receptor sites have been reviewed (Trends Neuroscience 1987; 10:444–446 and Clin. Neuropharmacol. 1988; 11:105). The structural determinants of sigma receptor affinity have been described (Mol. Pharmacol. 1987; 32:772–784 ). The compounds of the present invention have been found to have high affinity for the sigma site.

Sigma binding sites are found in the brain (J. M. Walker, et al, Pharmacol. Rev. 1990; 42:355) and have been implicated in a number of disease states such as psychosis and various motor disorders (dystonias and dyskinesia). For example, the mode of action of the potential antipsychotic rimcazole and BMY 14802 is believed to be related in part to an interaction through sigma sites (D. P. Taylor, et al, J. Drug Der. Res. 1987; 11:65). However, controversy exists as to the actual role of sigma sites in antipsychotic drug action (K. L. R. Jansen, Clin. Neuropharm. 1988; 11:565). High concentrations of sigma receptors are found in the red nucleus (RN), an area involved in posture and movement. It is reported that microinjection of sigma ligands to the RN of rats causes abnormal postural changes (dystonias) (J. M. Walker, et al, Neurology 1988; 8:961). Abnormal sigma binding patterns have been observed in brain from genetically dystonic rats (W. D. Bowen, et al, Eur. J. Pharmacol. 1988; 147:153). Also, certain steroids are naturally occurring ligands for the sigma binding site (T. Su, et al, Science 1988; 148:467), which raises the possibility that the sigma site may mediate some aspects of steroid-induced mental disturbances and alterations in immune functions. Further, sigma binding sites are found in spleen and lymphocytes (T. Su, et al, Eur. J. Pharmacol. 1988; 148:467 and S. A. Wolfe, et al, Soc. Neurosci. Abstr. 1987; 13: 1437 ), suggesting that sigma binding sites may play an important role in the immune system.

Since the sigma binding site was first postulated in 1976 (W. R. Martin, et al, J. Pharmacol. Exp. Ther. 1976; 197:517), a great number of studies have been carried out to discover its nature and function ( J. M. Walker, Pharmacol. Rev. 1990; 42:355). Despite the considerable amount of work, there are no known commercially available agonists or antagonists for the sigma binding sites. DuP 734 [1-(cyclopropylmethyl)-4-(2',4"-fluoroethyl)-2'-oxoethyl ) piperidine HBr] which has antipsychotic properties, is believed to be a sigma binding site antagonist (L. Cook, et al, Abstract 133.8, p. 333, Society for Neuroscience, 21st Annual Meeting, New Orleans, La., Nov. 10–15, 1991). The availability of selective sigma ligands is highly desirable as tools to further unravel the biological and pharmacological role played by sigma sites.

SUMMARY OF THE INVENTION

The present invention provides novel pharmaceutically useful tetrahydropyridine compounds having the following general Formulas I and II:

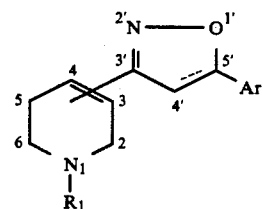

I

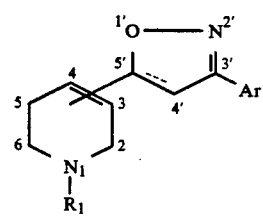

II wherein the dotted line between carbons 4' and 5' represents the presence or absence of a double bond. The isoxazole/isoxazoline ring is attached to either the 3- or 4-position of the tetrahydropyridine ring; Ar is 2-or 3-thienyl, phenyl, or phenyl substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro or $NR_3R_4$ wherein each of $R_3$ and $R_4$ is hydrogen or a straight or branched alkyl having from 1 to 4 carbon atom; $R_1$ is hydrogen, a straight or branched alkyl group having from 1 to 6 carbon atoms, a cycloalkylmethyl group wherein the cycloalkyl moiety has from 3 to 6 carbon atoms, phenyl$(CH_2)n$ wherein n is one or two and wherein the phenyl ring is unsubstituted or substituted with from 1 to 3 substituents selected from chlorine, bromine, fluorine, trifluoromethyl, hydroxy, straight or branched alkyl having from 1 to 4 carbon atoms, straight or branched alkoxy having from 1 to 4 carbon atoms, trifluoromethoxy, nitro or $-NR_3R_4$ are as defined above; and pharmaceutically acceptable salts thereof.

Compositions containing compounds of Formulas I and II are also included within the scope of the present invention as are novel methods of using the compounds and compositions. In particular, the present invention provides a method of treating depression in a mammal in need of such treatment comprising the administration of an antidepressant effective amount of a compound of Formula I or Formula II above in combination with a pharmaceutically acceptable carrier.

The present invention also provides a method of treating psychoses, e.g., schizophrenia, in a mammal in need of such treatment comprising the administration of an antipsychotic effective amount of a compound of Formulas I and II above in combination with a pharmaceutically acceptable carrier.

Additionally, the present invention provides a method of treating inflammation in a mammal in need of such treatment comprising the administration of an antiinflammatory effective amount of a compound of Formulas I and II above in combination with a pharmaceutically acceptable carrier.

Other novel utilities for the compounds of Formulas I and II are in the treatment of stroke, epilepsy, dystonias, anxiety, and diseases of the immune system.

The present invention also provides novel pharmaceutical compositions useful in treating the conditions enumerated above.

DETAILED DESCRIPTION OF INVENTION

In the above general Formulas I and II illustrative examples of straight or branched alkoxy groups having from 1 to 4 carbon atoms are methoxy, ethoxy, n-propoxy, isopropoxy, and n-butoxy. Illustrative examples of straight or branched alkyl groups having from 1 to 4 carbon atoms are methyl, ethyl, n-propyl, isopropyl, and n-butyl.

By virtue of the basic nitrogen atom in the tetrahydropyridine ring, the compounds of the present invention form pharmaceutically acceptable acid addition salts with organic and inorganic acids. Examples of suitable acids for the formation of pharmaceutically acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspattic, benzenesulfonic, methane-and ethanesulfonic, hydroxymethane, and hydroxyethanesulfonic, and the like (see, for example, "Pharmaceutical Salts" J Pharm. Sci 1977; 66(1) :1–19).

The compounds of Formulas I and II are prepared as set forth in Charts I and II hereof wherein the various symbols ----, Ar, and $R_1$ have the meanings defined in Formulas I and II. In Chart I 3(or 4)-pyridinealdoxime (1) is converted to corresponding nitrile oxide (2) in situ by reaction with sodium hapochloride and triethylamine. [3+2] Cycloaddition of (2) with arylacetylene (or arylethylene) affords isoxazole (or isoxazoline) (3). Alkylation of (3) with alkyl iodide in acetonitrile furnishes pyridinium salt (4). Reduction of (4) using sodium borohydride gives tetrahydropyridinylisoxazole (or tetrahydropyridinylisoxazoline) (5).

The compounds of the present invention as represented by general Formula I and II can also be synthesized through the general reaction scheme set forth in Chart II wherein the various substituents At, $R_1$ have the meanings defined in Formula I and Formula II.

Alternatively, 3(or 4)-acetopyridine (6) is condensed with methyl benzoates (7) in the presence of sodium hydride to give 1,3-diketone (8). Condensation of (8) with hydroxylamine hydrochloride affords a mixture of two isoxazoles (9) and (10). The mixture of (9) and (10) is reacted with alkyl halides in acetonitrile to furnish a mixture of two pyridinium salts (11) and (12). The mixture of (11) and (12) is reduced using sodium borohydride to give a mixture of two tetrahydropyridinylisoxazoles (13) and (14). The mixture is separated by column chromatography to give pure (13) and (14).

The specific examples set out below further illustrate the synthesis of the compounds of Formulas I and II.

The utility of the compounds of the present invention is demonstrated by various in vitro studies. Sigma binding affinities are measured using [$^3$H]-(+)-3-(3'-hydroxyphenyl)-N-(1'-propyl)-piperdine, referred to in the following Table I as 3PPP. This test is carried out according to the procedures of B. L. Largent, et al, Proc. Natl. Acad. Sci., USA, 1984; 81:5618. The ability of the compounds to bind muscarinic antagonist sites was determined invitro using [$^3$H]quinuclidinyl benzylate (RQNB) according to the procedure of M. Watson, J. Pharmacol. Exp. Ther. 1986; 237–411.

TABLE I

| Example Number | [$^3$H]PPP (IC$_{50}$ nM) | RQNB % Inhibition @ 1 μM |
|---|---|---|
| 1 | 7.05 | 10 |
| 2 | 39.1 | 7 |
| 3 | 1.03 | 22 |
| 4A | 0.78 | 10 |
| 4B | 8.80 | 4 |
| 5A | 0.067 | 10 |
| 5B | 0.62 | 6 |
| 6A | 4.00 | 15 |
| 6B | 0.10 | 7 |
| 7A | 0.45 | 10 |
| 7B | 9.90 | 10 |
| 8A | 3,643 | 40 |
| 8B | 546 | 12 |
| 14A | 10,000 | 11 |
| 14B | 1,475 | 9 |
| 9A | >10,000 | 23 |
| 9B | 10,000 | 12 |

In therapeutic use as agents for treating depression, psychoses, inflammation, dystonias, epilepsy, stroke, anxiety, and immune diseases, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

EXAMPLE 1

3-[3'-(1'-propyl-1', 2', 5', 6'-tetrahydropyridinyl)]-5-phenyl-2-isoxazoline (a) 3-(3'-pyridinyl)-5-phenyl-2-isoxazoline To a solution of 3-pyridinealdoxime (12.21 g, 0.10 mol), styrene (22.91 mL, 0.20 mol), and triethylamine (13.90 mL, 0.10 mol) in methylene chloride (300 mL) at 0° C. with stirring was added a 6% aqueous solution of sodium hypochloride (170.0 mL, 0.15 mol) dropwise over a period of 1.5 hours. The "mixture was stirred for an additional 2 hours at 0° C. The organic layer was separated. The aqueous layer was extracted with methylene chloride (200 mL×3). The combined organic layer was dried over anhydrous sodium sulfate. After the solvent and drying agent were removed, the crude product was purified on a dry-flash silica gel column ($CH_2Cl_2$ to 2% $CH_3OH$ in $CH_2Cl_2$) to give the title compound as yellowish liquid (13.18 g, 58.8%).

$^1H$ NMR ($CDCl_3$) δ3.36 (dd, J=8.4, 16.8 Hz, 1H), 3.80 (dd, J=11.0, 16.8 Hz, 1H), 5.80 (dd, J=8.4, 11.0 Hz, 1H), 7.31–7.40 (m, 6H), 8.10 (dt, j=1.7, 8.0 Hz, 1H), 8.65 (dd, J=1.7, 4.8 Hz, 1H), 8.83 (d, J=1.7 Hz, 1H). IR ($cm^{-1}$): 1590, 1450, 1369, 1028, 892, 743, 695. $^{13}C$ NMR ($CDCl_3$) δ 42.5, 83.0, 123.7, 125.8, 128.5, 128.9, 133.9, 140.4, 147.6, 150.9, 153.7. MS: m/e 225 (M+).

(b) 3-[3'-(1'-Propyl-1', 2', 5', 6'-tetrahydropyridinyl)]-5-phenyl,2-isoxazoline This reaction was carried out in two steps.

A: To a solution of 3-(3'pyridinyl)-5-phenyl-2-isoxazoline (11.75 g, 0. 050 mol) in acetonitrile (150 mL) at room temperature was added iodopropane (7.70 mL, 0.075 mol). The mixture was refluxed for 24 hours. The solvent volume was reduced to about 50 mL under vacuum followed by dilution with ethyl acetate (250 mL) to give yellow precipitate. The yellow solid (3-[3'-(1'-propylpyridinyl)]-5-phenyl-2-isoxazoline iodide) was then filtrated and washed with ethyl acetate (100 mL×3). The pyridinium salt (19.71 g, 100%) was used in the next step without further purification.

B: To a solution of 3-[3'-(1'-propylpyridinyl)]-5-phenyl-2-isoxazoline iodide (19.71 g, 0.05 mol) in a mixed solvent of methanol and water (200 mL, 1/1) at 0° C. with vigorous stirring was added sodium borohydride (3.78 g, 0.10 mol) in portion. The mixture was stirred for an additional 1 hour, and allowed to warm to room temperature. The solvent was removed to dryness under vacuum. The residue was dissolved in methylene chloride (200 mL) and aqueous sodium carbonate (saturated, 150 mL). The organic layer was separated. The aqueous layer was extracted with methylene chloride (200 mL×3). The combined organic layer was dried over anhydrous sodium sulfate. After solvent and drying agent were removed, the crude product was purified by medium-pressure liquid chromatography (silica gel, $CH_2Cl_2$ to 3% $CH_3OH$ in $CH_2Cl_2$) to furnish the title compound as yellowish oil. The title compound was converted to corresponding oxalic salt.

$^1H$ NMR (DMSO/TFA) δ 0.94 (t, J=7.3 Hz, 3H), 1.74 (m, 2H), 2.58 (m, 2H), 3.19 (m, 3H), 3.32 (m, 2H), 3.69 (m, 2H), 4.00 (bs, 2H), 5.69 (dd, J=8.2, 10.8 Hz, 1H), 6.38 (bs, 1H), 7.42 (m, 5H). $^{13}C$ NMR (DMSO/TFA) δ 11.0, 16.9, 22.6, 41.1, 47.0, 48.4, 50.9, 56.6, 81.8, 122.8, 126.0, 128.2, 128.6, 130.4, 140.7, 155.6, 164.0. IR to hygroscopic for IR. MS: m/e 270 (M+).

EXAMPLE 2

3-[3'-(1'-Propyl-1', 2', 5', 6'-tetrahydropyridinyl) ]-5-(4'-methoxyphenyl)-2 -isoxazoline When in the procedure of Example 1 (a) an appropriate amount of 4-methoxystyrene was substituted for styrene and the procedure of Examples 1 (a) and 1 (b) was followed, the title compound was obtained. $^1H$ NMR (DMSO/TFA) δ 0.94 (t, J=7.3 Hz, 3H), 1.73 (m, 2H), 2.58 (m, 2H), 3.08 (m, 2H), 3.15 (dd, J=8.7, 16.9 Hz, 1H), 3.28 (m, 2H), 3.61 (dd, J=10.6, 16.9 Hz, 1H), 3.78 (s, 3H), 3.96 (bs, 2H), 5.61 (dd, J=8.7, 10.6 Hz, 1H), 6.37 (bs, 1H), 6.97 (d, J=8.7 Hz, 2H), 7.30 (d, J=8.7 Hz, 2H). $^{13}C$ NMR (DMSO/TFA) δ 11.0, 17.0, 22.7, 40.8, 47.1, 48.5, 55.1, 56.8, 81.7, 114.0, 123.1, 127.6, 130.2, 132.3, 5.8, 159.2, 164.4. IR (cm$^-$): Too hygroscopic. MS: m/e 300 (M+)

EXAMPLE 3

3-[3'-(1'-Propyl-1', 2', 5', 6'-tetrahydropyridinyl)]-5-(4'-chlorophenyl)-2-isoxazoline When in the procedure of Example 1 (a) an appropriate amount of 4-chlorostyrene was substituted for styrene and the procedure of Examples 1 (a) and 1 (b) was followed, the title compound was obtained, m.p. 132°–134° C.

EXAMPLE 4

3-Phenyl-5-[3'-(1'-propyl-1', 2', 5', 6'-tetrahydropyridinyl)]isoxazole and 3-[3'-(1'propyl-1', 2', 5', 6'-tetrahydropyridinyl)]-5-phenylisoxazole (a) 1-{3'-Pyridinyl)-3-phenyl-1,3-propiodione To a suspension of sodium hydride (3.0 g, 60% in mineral oil, prewashed with anhydrous hexane) in 1,4-dioxane (50 mL) at room temperature was added methyl benzoate (neat, 3.11 mL, 0.025 mol). The mixture was heated to refluxing temperature (about 10° C.) followed by addition of a solution of 3-acetylpyridine (2.75 mL, 0. 025 mol) in 1,4-dioxane (20 mL) dropwise over a period of 30 minutes. The mixture was refluxed for an additional hour. After the reaction mixture was cooled to 0° C. with an ice-water bath, it was carefully quenched with water. Ethyl acetate (150 mL) and brine (200 mL) were added to the mixture. The pH of the aqueous was adjusted to 8 using diluted hydrochloric acid. The organic layer was separated. The aqueous layer was extracted with ethyl acetate (150 mL×3). The combined organic layer was dried over anhydrous sodium sulfate. After the drying agent and solvent were removed, the crude product was purified on a silica gel dry-flash column to give a yellow solid. The title compound was obtained as yellow needle-like crystal (4.11 g, 73.0% ) after recrystallization from ethyl acetate and hexane (1/4). m.p.: 120°–121° C.

(b) 3-(3'-Pyridinyl)-5-phenylisoxazole and 3-phenyl-5-(3'-pyridinyl)isoxazole

To a solution of 1-(3'-pyridinyl)-3-phenyl-1,3-propiodione (3.40 g, 0.015 mol) in methanol at room temperature was added hydroxylamine hydrochloride (2.09 g, 0. 030 mol). The mixture was refluxed for 12 hours. The solvent was removed to dryness under vacuum. The residue was dissolved in methylene chloride (150 mL) and aqueous sodium bicarbonate (saturated, 150 mL). The organic layer was separated. The aqueous layer was extracted with methylene chloride (100 mL×3). The combined organic layer was dried over anhydrous sodium sulfate. After the drying agent and solvent were removed, the crude product was purified on a dry-flash silica gel column to furnish a mixture of the two title compounds. (b) $^1$H NMR (CDCl$_3$) δ 6.87 (s, 1H), 6.93 (s, 1H), 7.49 (m, 8H), 7.86 (m, 4H), 8.13 (dt, J=2.1, 8.0 Hz, 1H), 8.20 (dt, J=1.8, 7.9 Hz, 1H), 8.70 (m, 2H), 9.08 (m, 2H). $^{13}$C NMR (CDCl$_3$) δ 97.1, 98.5, 123.8, 125.9, 126.9, 127.1, 128.7, 129.0, 129.1, 130.3, 130.6, 132.9, 134.0, 147.1, 148.0, 151.0, 151.1, 160.5, 163.1, 167.6, 171.1. IR (cm$^{-1}$): 1653, 1612, 1595, 1576, 1570, 1463, 1437, 1414. MS: m/e 222(M+).

(c) This reaction was carried out in two steps

To a solution of 3- (3'-pyridinyl)-5-phenylisoxazole and 3-phenyl-5-(3'-pyridinyl)isoxazole (3.80 g, 17.0 mmol) in ethyl acetate (50 mL) at room temperature was added iodopropane (4.87 mL, 50.0 mmol). The mixture was refluxed for 7 days. The pyridium salts were formed as yellow precipitate. The yellow solid (3-[3'-(1-propylpyridinyl)]-5-phenylisoxazole iodide and 3-phenyl-5-[3'-(1'-propylpyridinyl)isoxazole iodide) was then filtrated and washed with ethyl acetate (50 mL×3). The pyridinium salts (4.09 g, 61.4% ) were used in the next step without further purification, m.p. 216°–217° C.

To a solution of 3-[3'-(1'-propylpyridinyl)]-5-phenylisoxazole iodide and 3-phenyl-5-[3'-(1'-propylpyridinyl)isoxazole iodide (3.86 g, 9.45 mmol) in a mixed solvent of methanol and water (100 mL, 1/1) at 0° C. with vigorous stirring was added sodium borohydride (0.71 g, 18.9 mmol) in portion. The mixture was stirred for an additional 1 hour, and allowed to warm to room temperature. Solvent was removed to dryness under vacuum. The residue was dissolved in methylene chloride (100 mL) and aqueous sodium carbonate (saturated, 100 mL). The organic layer was separated. The aqueous layer was extracted with methylene chloride (100 mL×3). The combined organic layer was dried over anhydrous sodium sulfate. After solvent and drying agent were removed, the crude product was separated by medium-pressure liquid chromatography (silica gel, CH$_2$Cl$_2$ to 3% CH$_3$OH in CH$_2$Cl$_2$) to furnish the two title compounds as yellowish oil. They were converted to corresponding oxalic salts, m.p. 159°–162° C.

A: 3-phenyl-5-[3'-(1'-propyl-1', 2', 5', 6'-tetrahydropyridinyl)]isoxazole oxalate B: 3-[3'-(1'-propyl-1', 2', 5', 6'-tetrahydropyridinyl)]-5-phenylisoxazole oxalate When in the procedure of Example 4(a) an appropriate amount of the substituted methylbenzoate listed below in Table II was substituted for methylbenzoate and the procedure of Examples 4(a), 4(b), and 4(c) was followed, the respective products listed below were obtained.

TABLE II

| Example Number | Substituted Methylbenzoate | Product |
|---|---|---|
| 5 | p-methyl methylbenzoate | A. 3-(4'-Methylphenyl)-5-[3'-(1'-propyl-1', 2', 5', 6'-tetrahydropyridinyl)]isoxazole oxalate, m.p. 214–215° C. |
| | | B. 3-[3'-(1'-propyl-1', 2', 5', 6'-tetrahydropyridinyl)]-5-(4'-methylphenyl)isoxazole oxalate, m.p. 157–160° C. |
| 6 | m-methoxy methylbenzoate | A. 3-(3'-Methoxyphenyl)-5-[3'-(1'-propyl-1', 2', 5', 6'-tetrahydropyridinyl)]isoxazole oxalate, m.p. 175–177° C. |
| | | B. 3-[3'-(1'-propyl-1', 2', 5', 6'-tetrahydropyridinyl)]-5-(3'-methoxyphenyl)isoxazole oxalate, m.p. 186–188° C. |
| 7 | m-methyl methylbenzoate | A. 3-(3'-Methylphenyl)-5-[3'-(1'-propyl-1', 2', 5', 6'-tetrahydropyridinyl)]isoxazole oxalate, m.p. 221–222° C. |
| | | B. 3-[3'-(1'-propyl-1', 2', 5', 6'-tetrahydropyridinyl)]-5-(3'-methylphenyl)isoxazole oxalate, m.p. 154–156° C. |

TABLE II-continued

| Example Number | Substituted Methylbenzoate | Product |
|---|---|---|
| 8 | o-methyl methylbenzoate | A. 3-(2'-Methylphenyl)-5-[3'-(1'-propyl-1', 2', 5', 6'-tetrahydropyridinyl)]isoxazole oxalate, m.p. 213–215° C.<br>B. 3-[3'-(1'-propyl-1', 2', 5', 6'-tetrahydropyridinyl)]-5-(2'-methylphenyl)isoxazole oxalate, m.p. 166–168° C. |
| 9 | o-methoxy methylbenzoate | A. 3-(2'-Methoxyphenyl)-5-[3'-(1'-propyl-1', 2', 5', 6'-tetrahydropyridinyl)]isoxazole oxalate, m.p. 183–185° C.<br>B. 3-[3'-(1'-propyl-1', 2', 5', 6'-tetrahydropyridinyl)]-5-(2'-methoxyphenyl)isoxazole oxalate, m.p. 195–197° C. |
| 10 | p-chloro methylbenzoate | A. 3-(4'-Chlorophenyl)-5-[3'-(1'-propyl-1', 2', 5', 6'-tetrahydropyridinyl)]isoxazole oxalate, m.p. 213–215° C.<br>B. 3-[3'-(1'-propyl-1', 2', 5', 6'-tetrahydropyridinyl)]-5-(4'-chlorophenyl)isoxazole oxalate, m.p. 167–169° C. |
| 11 | m-chloro methylbenzoate | A. 3-(3'-Chlorophenyl)-5-[3'-(1'-propyl-1', 2', 5', 6'-tetrahydropyridinyl)]isoxazole oxalate, m.p. 218–219° C.<br>B. 3-[3'-(1'-propyl-1', 2', 5', 6'-tetrahydropyridinyl)]-5-(3'-chlorophenyl)isoxazole oxalate, m.p. 155–157° C. |
| 12 | o-chloro methylbenzoate | A. 3-(2'-Chlorophenyl)-5-[3'-(1'-propyl-1', 2', 5', 6'-tetrahydropyridinyl)]isoxazole oxalate, m.p. 207–208° C.<br>B. 3-[3'-(1'-propyl-1', 2', 5', 6'-tetrahydropyridinyl)]-5-(2'-chlorophenyl)isoxazole oxalate, m.p. 167–169° C. |
| 13 | 3,4-dichloro methylbenzoate | A. 3-(3', 4'-dichlorophenyl)-5-[3'-(1'-propyl-1', 2', 5', 6'-tetrahydropyridinyl)]isoxazole oxalate, m.p. 233–234° C.<br>B. 3-[3'-(1'-propyl-1', 2', 5', 6'-tetrahydropyridinyl)]-5-(3', 4'-dichlorophenyl)isoxazole oxalate, m.p. 200–201° C. |
| 14 | p-methoxy methybenzoate | A. 3-(4'-Methoxyphenyl)-5-[3'-(1'-propyl-1', 2', 5', 6'-tetrahydropyridinyl)]isoxazole oxalate, m.p. 213–215° C.<br>B. 3-[3'-(1'-propyl-1', 2', 5', 6'-tetrahydropyridinyl)]-5-(4'-methoxyphenyl)isoxazole oxalate, m.p. 166–168° C. |

Where in the procedure of Example 4(a) an appropriate amount of 4-methyl methylbenzoate is substituted for methylbenzoate and in the procedure of Example 4(c) an appropriate amount of the iodo-R compound listed in Table III is substituted for iodopropane and the procedure of Examples 4(a), 4(b), and 4(c) is followed, the products listed below were obtained.

TABLE III

| Example Number | iodo-R Compound | Product |
|---|---|---|
| 15 | iodomethane | A. 3-(4'-methylphenyl)-5-[3'-(1'-methyl-1', 2', 5', 6'-tetrahydropyridinyl)]isoxazole oxalate, m.p. 211–212° C.<br>B. 3-[3'-(1'-methyl-1', 2', 5', 6'-tetrahydropyridinyl)]-5-(4'-methylphenyl)isoxazole oxalate, m.p. 170–171° C. |
| 16 | 1-iodo-2-phenylethane | A. 3-(4'-methylphenyl)-5-(3'-[1'-(2''-phenylethyl)-1', 2', 5', 6'-tetrahydropyridinyl])isoxazole oxalate, m.p. 224–225° C.<br>B. 3-(3'-[1'-(2''-phenylethyl)-1', 2', 5', 6'-tetrahydropyridinyl)]-5-(4'-methylphenyl)isoxazole oxalate, m.p. 222–223° C. |
| 17 | iodopentane | A. 3-(4'-methylphenyl)-5-[3'-(1'-pentyl-1', 2', 5', 6'-tetrahydropyridinyl)]isoxazole oxalate, m.p. 214–216° C.<br>B. 3-[3'-(1'-pentyl-1', 2', 5', 6'-tetrahydropyridinyl)]-5-(4'-methylphenyl)isoxazole oxalate, m.p. 162–164° C. |
| 18 | iodoethane | A. 3-(4'-methylphenyl)-5-[3'-(1'-ethyl-1', 2', 5', 6'-tetrahydropyridinyl)]isoxazole oxalate, m.p. 226–227° C.<br>B. 3-[3'-(1'-ethyl-1', 2', 5', 6'-tetrahydropyridinyl)]-5-(4'-methylphenyl)isoxazole oxalate, m.p. 185–186° C. |
| 19 | iodomethylbenzene | A. 3-(4'-methylphenyl)-5-[3'-(1'-benzyl-1', 2', 5', 6'-tetrahydropyridinyl)]isoxazole oxalate, m.p. 198–199.5° C. |

TABLE III-continued

| Example Number | iodo-R Compound | Product |
|---|---|---|
| | | B. 3-[3'-(1'-benzyl-1', 2', 5', 6'-tetrahydropyridinyl)]-5-(4'-methylphenyl)isoxazole oxalate, m.p. 229–231° C. |
| 20 | iodomethylcyclopropane | A. 3-(4'-methylphenyl)-5-[3'-(1-cyclopropylmethyl-1', 2', 5', 6'-tetrahydropyridinyl)]isoxazole oxalate, m.p. 214–215° C. |
| | | B. 3-[3'-(1'-cyclopropylmethyl-1', 2', 5', 6'-tetrahydropyridinyl)]-5-(4'-methylphenyl)isoxazole oxalate, m.p. 178–179° C. |
| 21 | iodo-2-propene | A. 3-(4'-methylphenyl)-5-[3'-(1'-allyl-1', 2', 5', 6'-tetrahydropyridinyl)]isoxazole oxalate, m.p. 216–217° C. |
| | | B. 3-[3'-(1'-allyl-1', 2', 5', 6'-tetrahydropyridinyl)]-5-(4'-methylphenyl)isoxazole oxalate, m.p. 165–169° C. |
| 22 | iodobutane | A. 3-(4'-methylphenyl)-5-[3'-(1'-butyl-1', 2', 5', 6'-tetrahydropyridinyl)]isoxazole oxalate, m.p. 222–223° C. |

CHART I

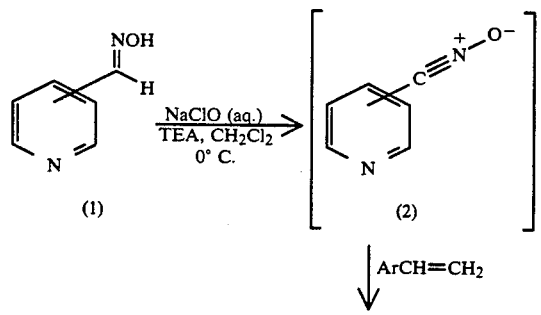

-continued
CHART I

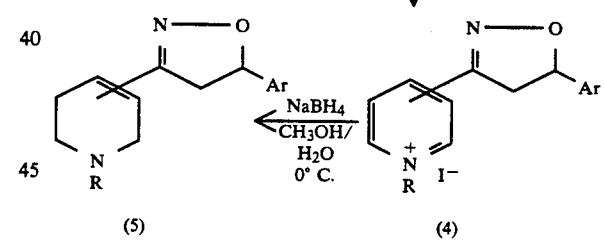

CHART II

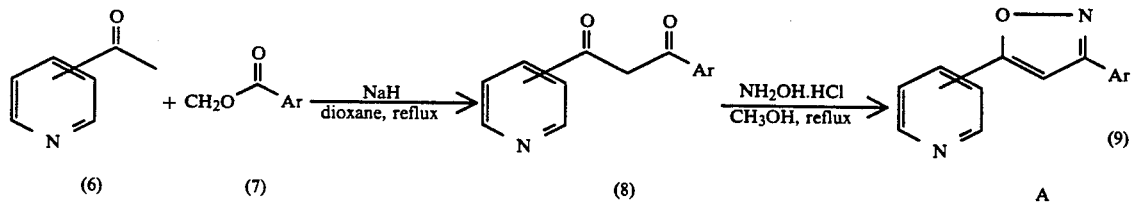

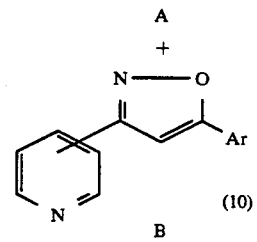

-continued
CHART II

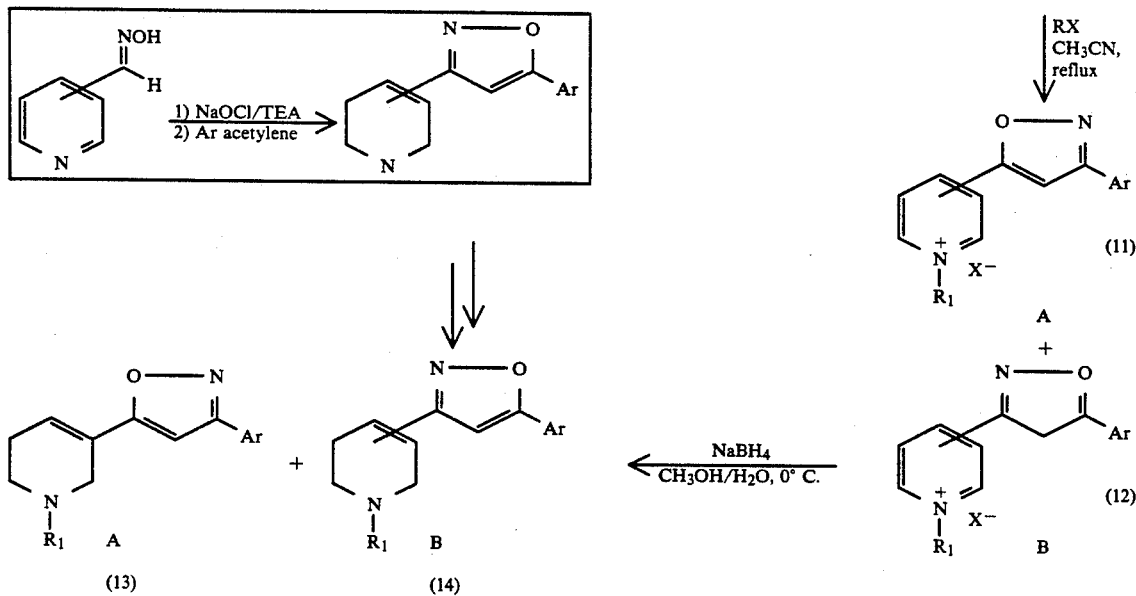

I claim:
1. A compound selected from the following Formula I or Formula II

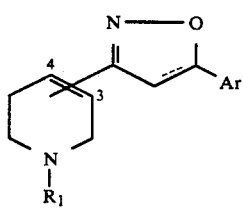 I

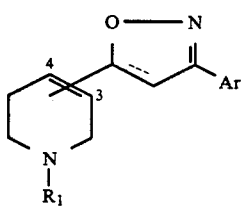 II wherein the dotted line represents the presence or absence of a double bond;
wherein the isoxazole/isoxazoline ring is attached to either the 3- or 4-position of the tetrahydropyridine ring;
wherein Ar is 2- or 3-thienyl, or phenyl substituted with from 1 to 3 substituents selected from chlorine, bromine, fluorine, trifluoromethyl, hydroxy, straight or branched alkoxy having from 1 to 4 carbon atoms, trifluoromethoxy, nitro, or $NR_3R_4$ wherein each of $R_3$ and $R_4$ is hydrogen or alkyl having from 1 to 4 carbon atoms;
wherein $R_1$ is hydrogen, a straight or branched alkyl group having from 1 to 6 carbon atoms, a cycloalkylmethyl group wherein the cycloalkyl moiety has from 3 to 6 carbon atoms, phenyl($CH_2$)$_n$— wherein n is one or two and the phenyl ring is unsubstituted, or is substituted with from 1 to 3 substituents selected from chlorine, bromine, fluorine, trifluoromethyl, hydroxy, straight or branched alkoxy having from 1 to 4 carbon atoms, straight or branched alkyl having from 1 to 4 carbon atoms, trifluoromethoxy, nitro, or —$NR_3R_4$ wherein $R_3$ and $R_4$ are as defined above; and pharmaceutically acceptable salts thereof.

2. A compound of claim 1 having the formula

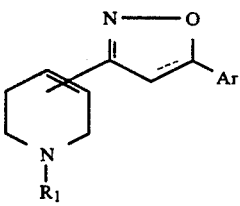

wherein Ar, $R_1$, and --- are as defined in claim 1.
3. A compound of claim 1 wherein the oxazoline ring is attached to the 3-position of the tetrahydropyridine ring.
4. A compound of claim 3 which is selected from:
3-[3'-(1'-propyl-1', 2', 5', 6 '-tetrahydropyridinyl)]-5-(4'-methoxyphenyl) -2-isoxazoline; and
3-[3'-(1'-propyl-1', 2', 5', 6'-tetrahydropyridinyl)]-5-(4'-chlorophenyl) -2-isoxazoline.
5. A compound of claim 2 wherein --- represents the presence of a double bond.
6. A compound of claim 5 which is selected from:
3-[3'-(1'-propyl-1', 2', 5', 6'-tetrahydropyridinyl)]-5-(3'-methoxyphenyl)isoxazole oxalate;
3-[3'- (1'-propyl-1', 6'-tetrahydropyridinyl)]-5- (4'-methoxyphenyl) isoxazole oxalate;
3-[3'-(1'-propyl-1', 2', 5', 6'-tetrahydropyridinyl)]-5-(2'-methoxyphenyl) isoxazole oxalate;
3-[3'-(1'-propyl-1', 2', 5', 6'-tetrahydropyridinyl)]-5-(4'-chlorophenyl)isoxazole oxalate;
3-[3'-(1'-propyl-1', 2', 5', 6'-tetrahydropyridinyl)]-5-(3'-chlorophenyl ) isoxazole oxalate;
3-[3'-(1'-propyl-1', 2', 5', 6'-tetrahydropyridinyl)]-5-(2'-chlorophenyl) isoxazole oxalate;

3-[3'-(1'-propyl-1', 2', 5', 6'-tetrahydropyridinyl)]-5-(3',4'-dichlorophenyl)isoxazole oxalate.

7. A compound of claim 1 having the formula

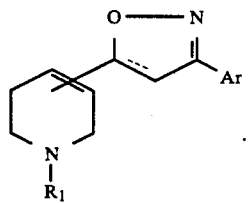

8. A compound of claim 7 wherein --- represents the presence of a double bond.

9. A compound of claim 8 which is selected from:

3-(3'-methoxyphenyl)-5-[3'-(1'-propyl-1', 2', 5', 6'-tetrahydropyridinyl)]isoxazole oxalate;

3-(4'-methoxyphenyl)-5-[3'-(1'-propyl-1', 2', 5', 6'-tetrahydropyridinyl)]isoxazole oxalate;

3-(2'-methoxyphenyl)-5-[3'-(1'-propyl-1', 2', 5', 6'-tetrahydropyridinyl)]isoxazole oxalate;

3-(4'-chlorophenyl)-5-[3'-(1'-propyl-1', 2', 5', 6'-tetrahydropyridinyl)]isoxazole oxalate;

3-(3'-chlorophenyl)-5-[3'-(1'-propyl-1', 2', 5', 6'-tetrahydropyridinyl)]isoxazole oxalate;

3-(2'-chlorophenyl)-5-[3'-(1'-propyl-1', 2', 5', 6'-tetrahydropyridinyl)]isoxazole oxalate;

3-(3', 4'-dichlorophenyl)-5-[3'-(1'-propyl-1', 2', 5', 6'-tetrahydropyridinyl)]isoxazole oxalate.

10. A pharmaceutical composition comprising an effective amount of a compound of claim 1 together with a pharmaceutically acceptable carrier.

11. A method of treating a patient having a central nervous system condition selected from depression, and anxiety which comprises administering to said patient an effective amount of a compound of claim 1.

12. A compound selected from the group consisting of

3-[3'-(1'-cyclopropylmethyl-1',2',5',6'-tetrahydropyridinyl)]-5(4'-methylphenyl)-isoxzaole oxalate;

3-[3'-(1'-allyl-1',2',5',6'-tetrahydropyridinyl)]-5-(4'-methylphenyl)-isoxzaole oxalate;

3- [3'(1'-benzyl-1', 2', 5', 6'-tetrahydropyridinyl)]-5-[4'-methylphenyl)isoxazole oxalate;

3-(4'-methylphenyl)-5-(3'-[1'-(2"-phenylethyl)-1',2',5',6'-tetrahydropyridinyl)]isoxazole oxalate; and 3-(4'-methylphenyl)-5-[3'-(1'-benzyl-1',2',5',6'-tetrahydropyridinyl)]isoxazole oxalate.

* * * * *

UNITED STATES PATENT AND TRADEMARK OFFICE
CERTIFICATE OF CORRECTION

PATENT NO. : 5,330,994
DATED : July 19, 1994
INVENTOR(S) : Pei et al

It is certified that error appears in the above-indentified patent and that said Letters Patent is hereby corrected as shown below:

Column 14, line 59, "3-[3'(1'-propyl-1',6'-" should read "3-[3'(1'-propyl-1',2',5',6'-".

Column 16, line 17, "-isoxzaole" should read "-isoxazole".

Column 16, line 20, "-isoxzaole" should read "-isoxazole".

Signed and Sealed this

Eleventh Day of October, 1994

Attest:

BRUCE LEHMAN

Attesting Officer

Commissioner of Patents and Trademarks